(12) United States Patent
Pruett

(10) Patent No.: US 9,055,991 B2
(45) Date of Patent: Jun. 16, 2015

(54) FLOSSING SYSTEM

(71) Applicant: Timothy J. Pruett, Tavares, FL (US)

(72) Inventor: Timothy J. Pruett, Tavares, FL (US)

(*) Notice: Subject to any disclaimer, the term of this patent is extended or adjusted under 35 U.S.C. 154(b) by 0 days.

(21) Appl. No.: 13/888,335

(22) Filed: May 6, 2013

(65) Prior Publication Data

US 2013/0239986 A1  Sep. 19, 2013

Related U.S. Application Data

(63) Continuation-in-part of application No. 13/343,756, filed on Jan. 9, 2012, now Pat. No. 8,517,074, which is a continuation-in-part of application No. 13/065,228, filed on Mar. 17, 2011, now Pat. No. 8,590,546, application No. 13/888,335, which is a continuation-in-part of application No. PCT/US2012/029187, filed on Mar. 15, 2012.

(51) Int. Cl.
*A61C 15/04* (2006.01)
*A46B 15/00* (2006.01)

(52) U.S. Cl.
CPC ........... *A61C 15/047* (2013.01); *A46B 15/0071* (2013.01); *A61C 15/048* (2013.01)

(58) Field of Classification Search
CPC ... A61C 15/046; A61C 15/047; A61C 15/048
USPC ................. 132/321–327, 329, 309; 15/167.1, 15/207.2; 206/63.5
See application file for complete search history.

(56) References Cited

U.S. PATENT DOCUMENTS

| | | | | | |
|---|---|---|---|---|---|
| 3,065,480 | A | * | 11/1962 | Sexton | 15/172 |
| 4,006,750 | A | * | 2/1977 | Chodorow | 132/323 |
| 4,399,582 | A | * | 8/1983 | Ernest et al. | 15/176.4 |
| 4,615,349 | A | * | 10/1986 | Kukuruzinski | 132/323 |
| 5,010,906 | A | * | 4/1991 | Preciutti | 132/323 |
| 5,170,809 | A | * | 12/1992 | Imai et al. | 132/322 |
| 5,267,579 | A | * | 12/1993 | Bushberger | 132/322 |
| 5,483,982 | A | * | 1/1996 | Bennett et al. | 132/323 |
| 5,722,440 | A | * | 3/1998 | Urso | 132/323 |
| RE36,699 | E | * | 5/2000 | Murayama | 433/118 |
| 6,067,684 | A | * | 5/2000 | Kweon | 15/167.1 |
| 6,382,219 | B1 | * | 5/2002 | Jelten | 132/323 |
| 6,397,858 | B1 | * | 6/2002 | Cubillo-Buron | 132/308 |
| 7,140,373 | B2 | * | 11/2006 | Rehkemper | 132/322 |
| 7,174,904 | B2 | * | 2/2007 | Ochs et al. | 132/323 |
| 7,325,554 | B2 | * | 2/2008 | Ochs | 132/323 |
| 7,392,810 | B2 | * | 7/2008 | Apotheker et al. | 132/323 |

(Continued)

FOREIGN PATENT DOCUMENTS

TW        M421096       *  1/2012     ............. A61C 15/04
WO   WO 2007061384 A1 *  5/2007     ............. A61C 15/00

*Primary Examiner* — Robyn Doan
*Assistant Examiner* — Tatiana Nobrega

(57) ABSTRACT

A handle has distal and proximal ends and a drive mechanism. Operational components on the handle include ON and OFF controls and a vibrating coupler to create sonic vibrations. A coupling head has a distal and a proximal ends. The proximal end is formed with a coupling recess. A replaceable holder has a central base and two outwardly extending fingers. The fingers have free ends with a piece of floss secured there between. The central base has a shape for coupling to and uncoupling from the coupling head. The length of the floss between the fingers is from 5 to 10 percent greater than the distance between the fingers. A compressible stop is on the base of the holder between the fingers. The remainder of the fingers are devoid of a compressible stop.

5 Claims, 9 Drawing Sheets

(56) References Cited

U.S. PATENT DOCUMENTS

| | | | |
|---|---|---|---|
| 7,487,785 B2* | 2/2009 | Dougan et al. | 132/323 |
| 2004/0079384 A1* | 4/2004 | Lai et al. | 132/322 |
| 2005/0076933 A1* | 4/2005 | Getgey et al. | 132/322 |
| 2005/0205107 A1* | 9/2005 | Ochs | 132/323 |
| 2006/0054180 A1* | 3/2006 | Getgey et al. | 132/322 |
| 2006/0174911 A1* | 8/2006 | Naruse | 132/322 |
| 2007/0054240 A1* | 3/2007 | Masterman et al. | 433/118 |
| 2008/0092917 A1* | 4/2008 | Getgey et al. | 132/322 |
| 2009/0165814 A1* | 7/2009 | Welt et al. | 132/323 |
| 2009/0293212 A1* | 12/2009 | Junkins | 15/22.1 |
| 2012/0021382 A1* | 1/2012 | Dickie | 433/216 |
| 2013/0061868 A1* | 3/2013 | Chuang | 132/323 |

* cited by examiner

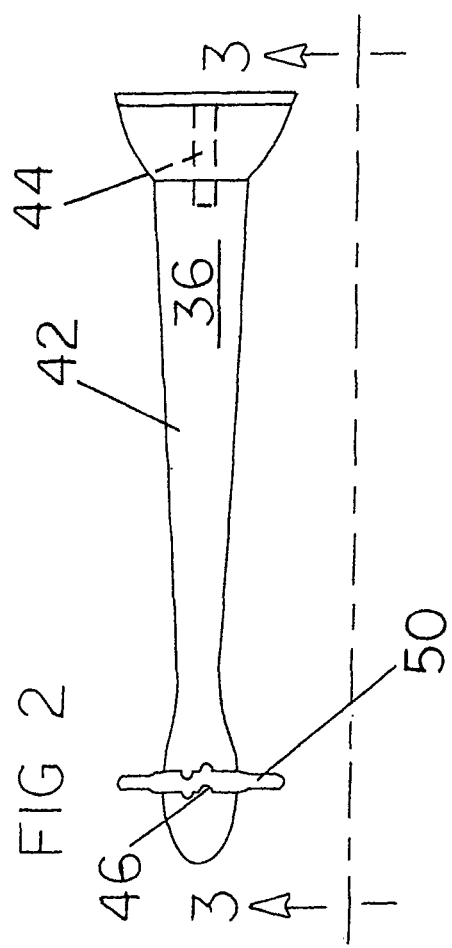
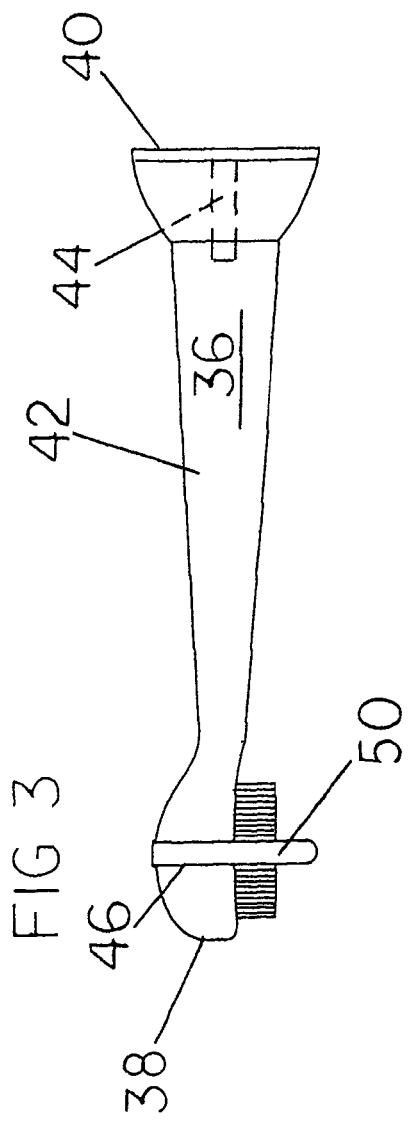

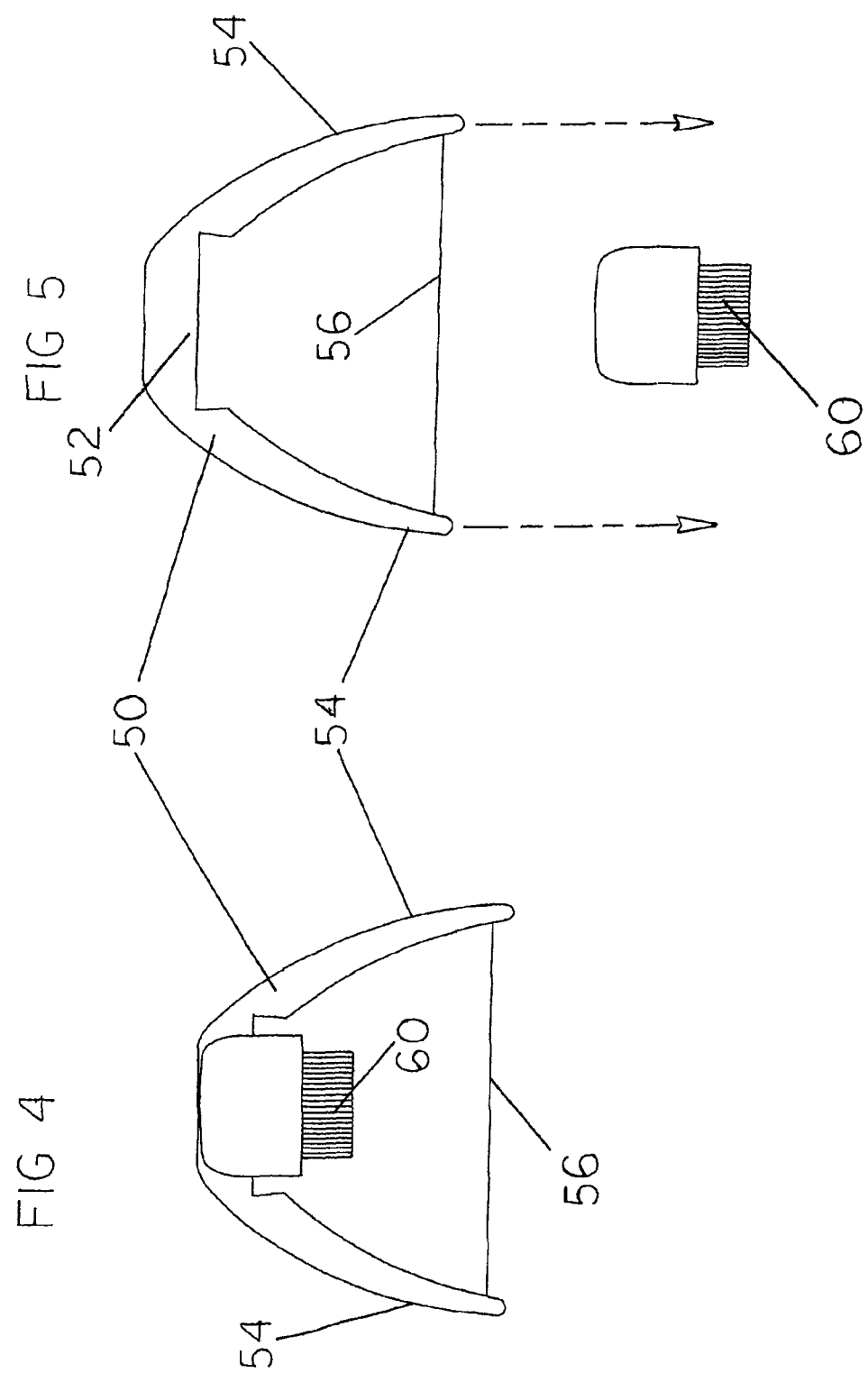

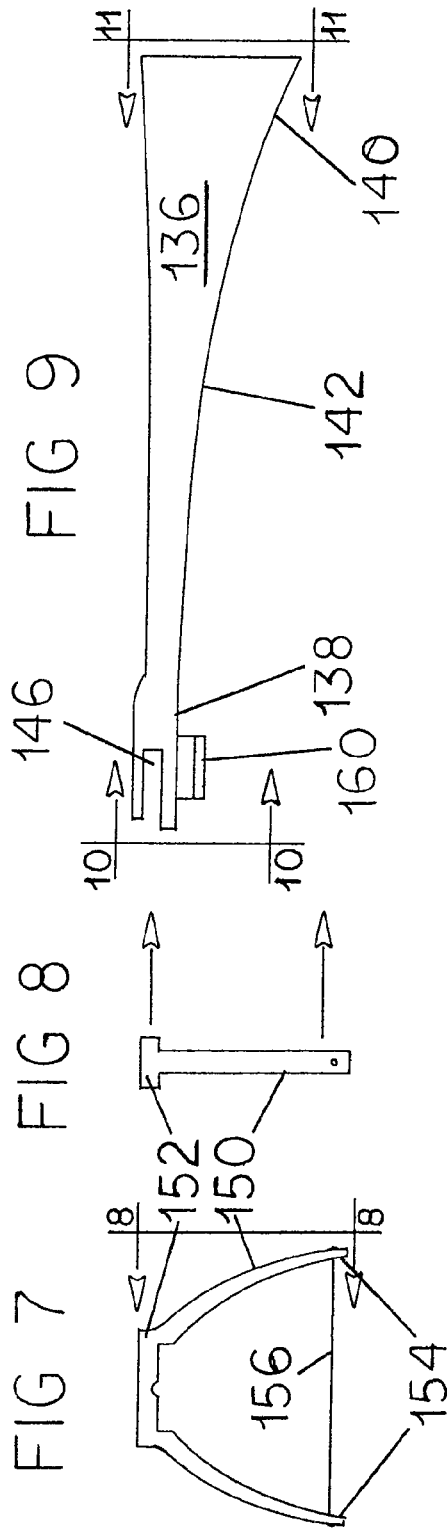

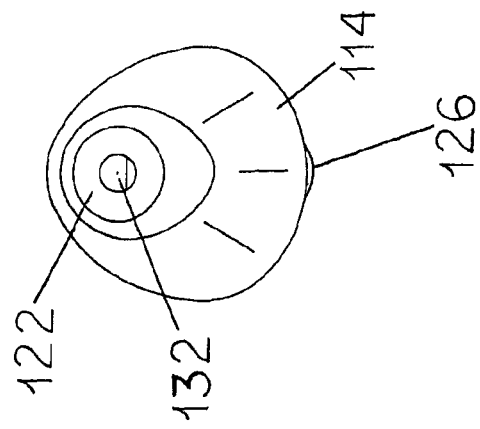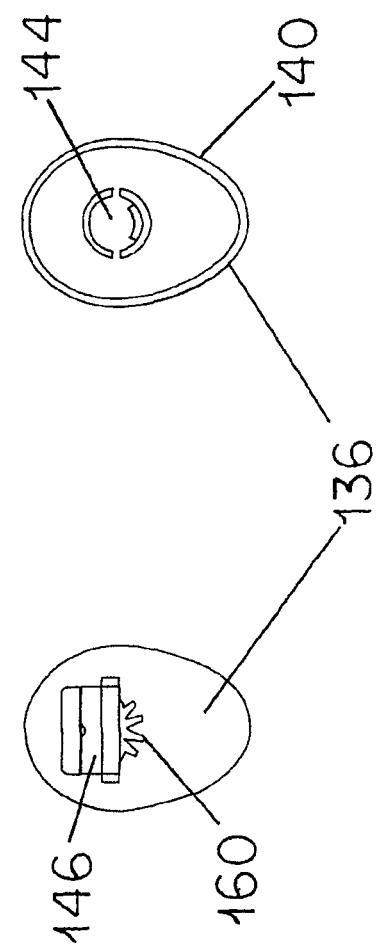

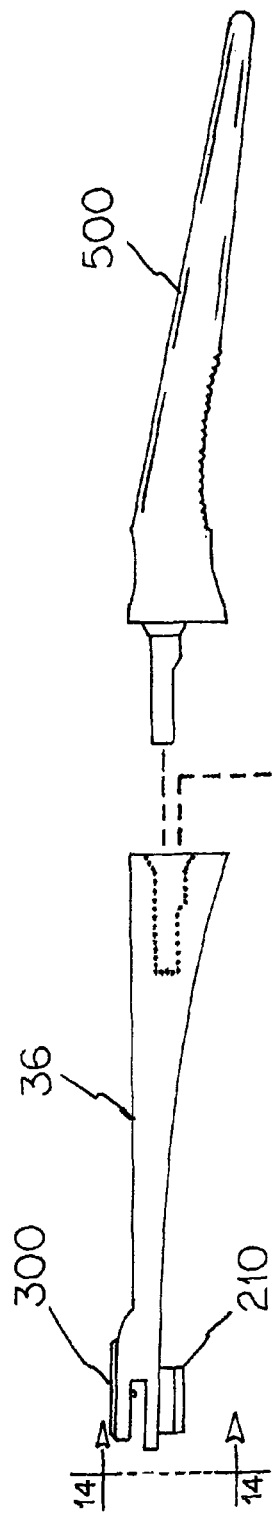
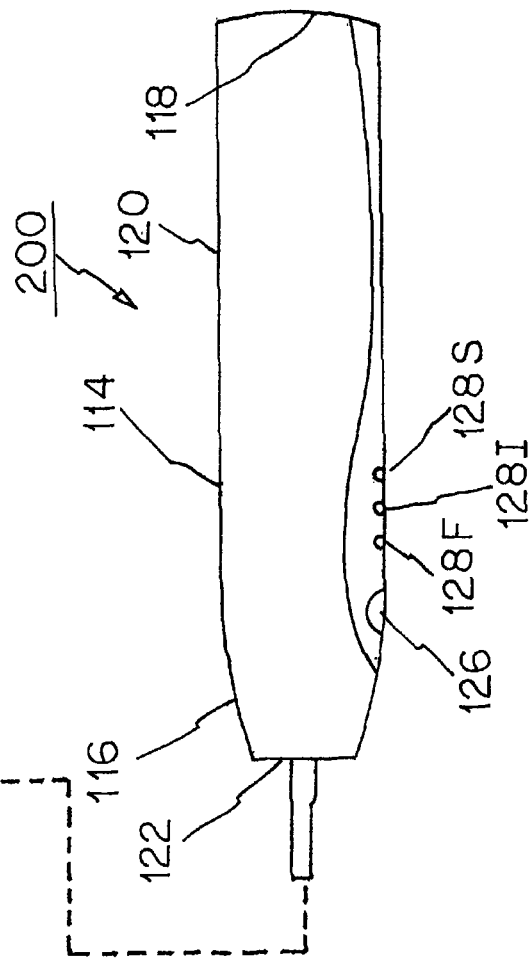
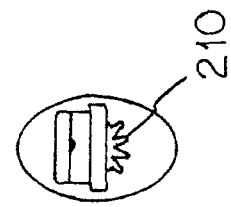
FIG. 13
FIG. 14

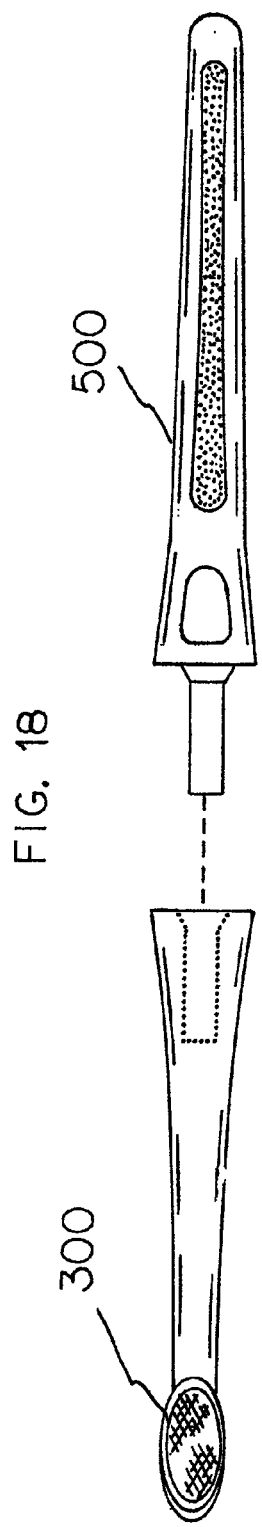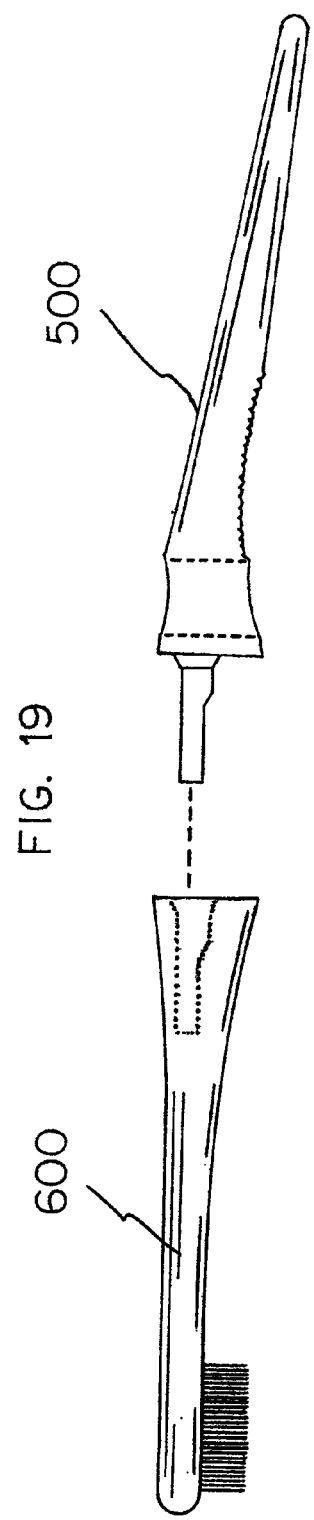

FLOSSING SYSTEM

RELATED APPLICATIONS

The present application is a continuation-in-part of abandoned application Ser. No. 13/343,756 filed Jan. 5, 2012 which, in turn, is a continuation-in-part of application Ser. No. 13/065,228 filed Mar. 17, 2011 which issued Nov. 26, 2013 as U.S. Pat. No. 8,590,546, and the present application is a continuation-in-part of PCT/US12/29187 filed Mar. 15, 2012, the subject matter of which applications is incorporated herein by reference.

BACKGROUND OF THE INVENTION

Field of the Invention

The present invention relates to a flossing system and more particularly pertains to cleaning teeth at regions between adjacent teeth of a user and for vibrating regions of the mouth of the user between teeth and gums, the cleaning and vibrating being done in a safe, painless, convenient, efficient and economical manner.

SUMMARY OF THE INVENTION

In view of the disadvantages inherent in the known types of teeth cleaning systems of known designs and configurations now present in the prior art, the present invention provides an improved flossing system. As such, the general purpose of the present invention, which will be described subsequently in greater detail, is to provide a new and improved flossing system and method which has all the advantages of the prior art and none of the disadvantages.

To attain this, the present invention essentially comprises a flossing system. A handle has distal and proximal ends and a drive mechanism. Operational components on the handle include ON and OFF controls and a vibrating coupler to create sonic vibrations. A coupling head has a distal and a proximal ends. The proximal end is formed with a coupling recess. A replaceable holder has a central base and two outwardly extending fingers. The fingers have free ends with a piece of floss secured there between. The central base has a shape for coupling to and uncoupling from the coupling head. The length of the floss between the fingers is from 5 to 10 percent greater than the distance between the fingers. A compressible stop is on the base of the holder between the fingers. The remainder of the fingers are devoid of a compressible stop.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved flossing system which has all of the advantages of the prior art teeth cleaning systems of known designs and configurations and none of the disadvantages.

It is another object of the present invention to provide a new and improved flossing system which may be easily and efficiently manufactured and marketed for both new handles with vibration generating drive mechanisms not currently on the market or otherwise known and existing handles with vibration generating drive mechanisms currently on the market.

It is further object of the present invention to provide a new and improved flossing system which is of durable and reliable constructions.

An even further object of the present invention is to provide a new and improved flossing system which is susceptible of a low cost of manufacture with regard to both materials and labor, and which accordingly is then susceptible of low prices of sale to the consuming public, thereby making such flossing system economically available to the buying public.

Even still another object of the present invention is to provide a flossing system for cleaning teeth at regions between adjacent teeth of a user and for vibrating regions of the mouth of the user between teeth and gums, the cleaning and vibrating being done in a safe, painless, convenient, efficient and economical manner.

Lastly, it is an object of the present invention to provide a new and improved flossing system for cleaning teeth at regions between adjacent teeth of a user and for vibrating regions of the mouth of the user between teeth and gums, the cleaning and vibrating being done in a safe, painless, convenient, efficient and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a rear elevational view of the flossing system shown in FIG. 1.

FIG. 3 side elevational view of the system taken along line 3-3 of FIG. 2.

FIG. 4 is an enlarged end elevational view of the head of the system of the prior Figures.

FIG. 5 is an exploded enlarged end elevational view of the head of the system of FIG. 4.

FIG. 7 is a front elevational view of the holder shown in FIG. 6.

FIG. 8 is an end elevational view taken along line 8-8 of FIG. 7.

FIG. 9 is a front elevational view of the holder shown in FIG. 6.

FIGS. 10-12 are end elevational views taken along lines 5-5, 6-6 and 7-7 of FIGS. 9 and 6.

FIG. 13 is a perspective view similar to FIG. 6 but illustrating the preferred embodiment of the invention.

FIG. 14 is a front elevational view taken along line 14-14 of FIG. 13.

FIG. 18 is a perspective illustration of a manual handle adapted for use as a substitute for the sonic handle of the primary embodiment.

FIG. 19 is a perspective illustration of a manual handle adapted for use with a brush arm to function as a tooth brush.

The same reference numerals refer to the same parts throughout the various Figures.

DESCRIPTION OF THE PREFERRED EMBODIMENT

Figure 1:
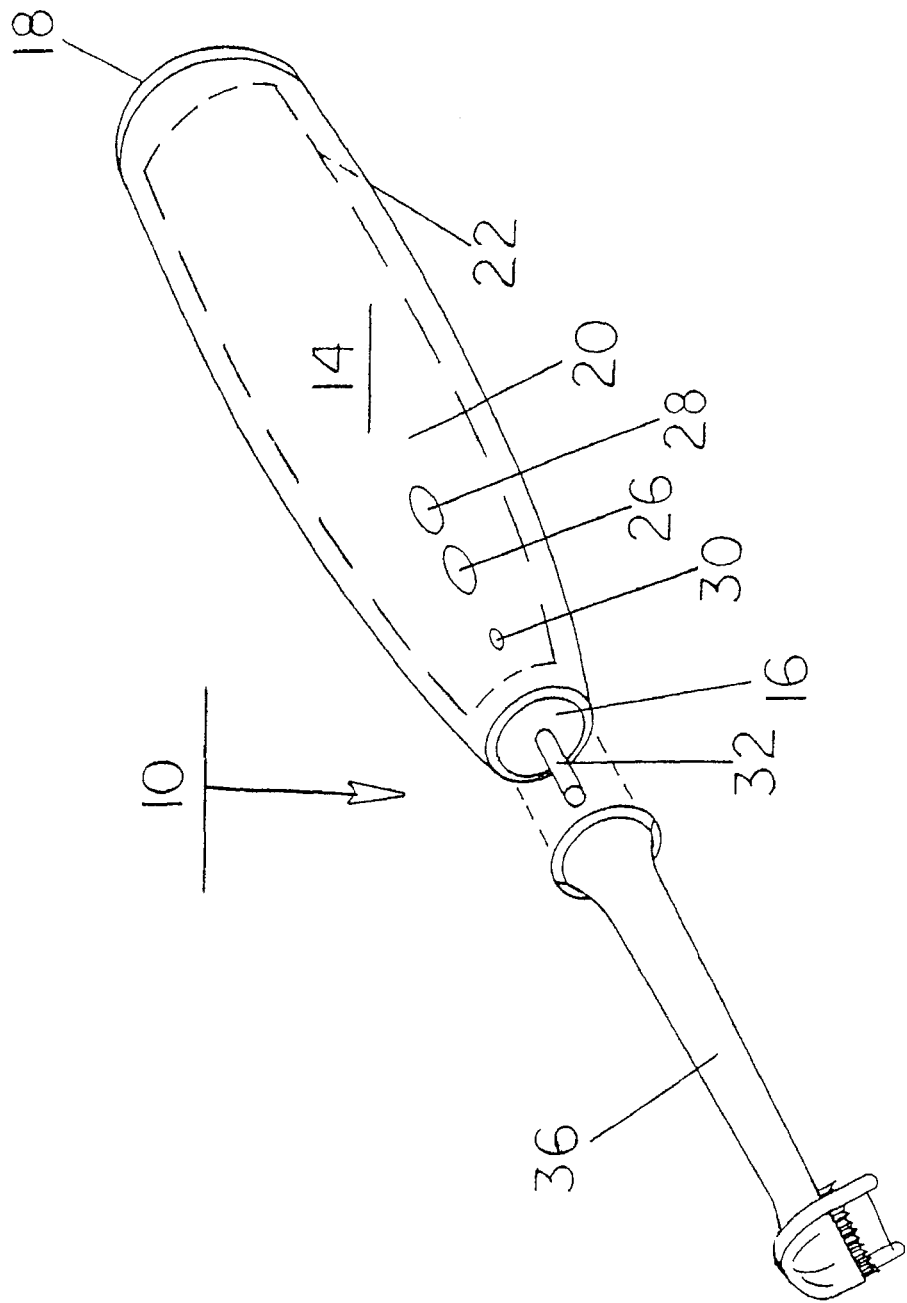
FIG. 1 is an exploded perspective illustration of a flossing system constructed in accordance with the principles of the present invention.
Figure 6:
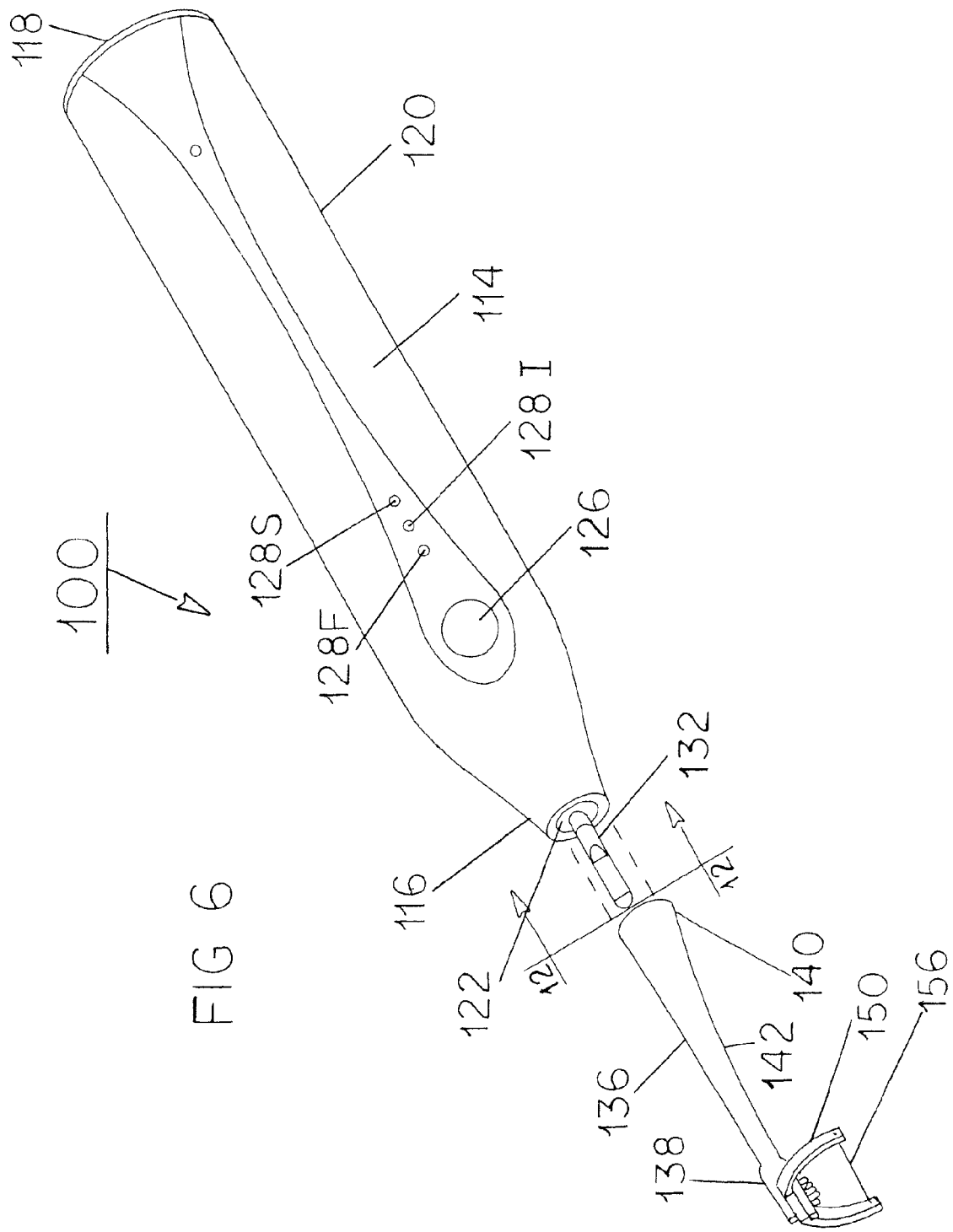
FIG. 6 is an exploded perspective illustration of a flossing system constructed in accordance with an alternate embodiment of the invention.
Figure 16:
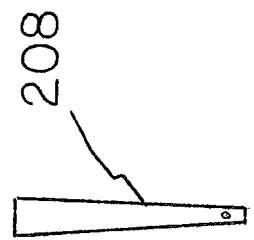
FIGS. 15 and 16 are enlarged front and side elevational views of the replaceable holders.
Figure 15:
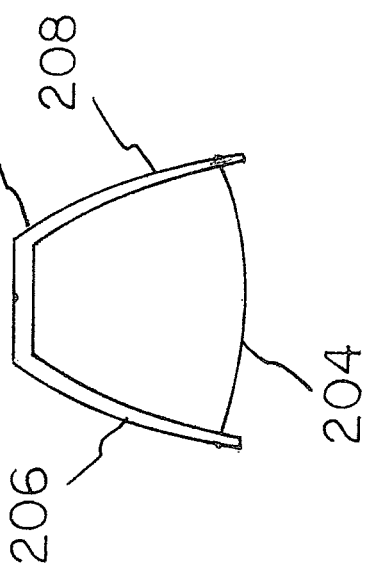

With reference now to the drawings, and in particular to FIG. 1 thereof, the preferred embodiment of the new and improved flossing system embodying the principles and concepts of the present invention and generally designated by the reference numeral 10 will be described.

The present invention, the flossing system 10 is comprised of a plurality of components. Such components in their broadest context include a handle, controls, a coupling head, a holder and bristles. Such components are individually configured and correlated with respect to each other so as to attain the desired objective.

First provided is a handle 14. The handle is in a generally cylindrical configuration. The handle has a distal end 16. The handle has a proximal end 18. The handle has an exterior surface 20. The exterior surface is provided between the distal and proximal ends. A vibration generating drive mechanism 22 with is provided. The vibration generating drive mechanism is provided within the handle. The vibration generating drive mechanism has a battery.

Operational components are provided on the handle. The operational components include an ON button 26. The operational components include an OFF button 28. The operational components also include an IN-USE light 30. The IN-USE light is provided on the exterior surface of the handle adjacent to the distal end. The operational components also include a vibrating coupler 32. The vibrating coupler is adapted to vibrate rapidly in a sonic range of 100 Hz and 500 Hz, preferably in a sonic range of 150 Hz and 300 Hz during use upon depressing the ON button.

Numerous vibration generating drive mechanisms were tested. Effective results were realized when operating in a sonic range of 100 Hz or 6,000 vibration oscillations per minute and 500 Hz or 30,000 vibration oscillations per minute. This in effect equates to a functional range of 12,000 flossing strokes per minute to 60,000 flossing strokes per minute, as one flossing stroke is equal to half of a vibration oscillation. This functional range is engaged by the flossing system with the adjustment of the power settings on the handle. The most effective range was preferably in a sonic range of 150 Hz and 300 Hz.

Provided next is a coupling head 36. The head is in a generally cylindrical configuration. The head has an enlarged distal end 38. The head has an enlarged proximal end 40. The head has an exterior surface 42. The exterior surface is provided between the enlarged distal and enlarged proximal ends. The enlarged proximal end has a coupling recess 44. A vibrating coupler 32 is provided. In this manner the coupling recess receives the vibrating coupler. The enlarged distal end has a planar surface forwardly. The enlarged distal end has a curved surface rearwardly. The curved surface has a transversely extending recess 46. The transversely extending recess is in a retentive configuration to removably receive and retain the replaceable holder 50, which exists as its reciprocal in shape.

Further provided is a replaceable holder 50. The replaceable holder has a central base 52. The central base has the reciprocal retentive shape of the rearwardly facing transverse recess 46 of the head to which the holder will be removably received. The replaceable holder has two outwardly extending fingers 54. The fingers have free ends. A piece of floss 56 is provided. The piece of floss is secured between the free ends. The head and the holder are fabricated of a plastic material. The plastic material has limited flexibility and resilience whereby applying pressure, note FIG. 5, to the central base of the holder toward the retentive recess 46 of the head will couple and secure the holder with respect to the head and whereby applying pressure in an opposite direction to the free ends of the fingers will allow uncoupling of the holder with respect to the head. The fingers are spaced from each other by between 0.50 and 1.00 inches. The floss is spaced from the base of the holder by between 0.40 and 0.75 inches. In this manner the floss is allowed to be positioned between teeth being flossed with the teeth between the fingers.

Provided last are bristles 60. The bristles extend from the planar surface of the base between the fingers. The bristles have a length of between 0.125 and 0.250 inches. The bristles are adapted to contact ends of teeth being flossed. In this manner the bristles function as a stop to control the depth of penetration of the floss between the teeth while the ON button has been depressed and the head is vibrating during flossing.

The releasable coupling between the recess 46 and the base 52 of the holder 50 is illustrated as being achieved through lines in a zig-zag or Z-shaped configuration. It should be understood, however, that the recess and the base of the holder could readily take any of a wide variety of complimentary configurations whereby they would still achieve their coupling and uncoupling function.

An alternate embodiment of the invention is illustrated in FIGS. 6-12. In such alternate embodiment, a flossing system 100 is provided for cleaning teeth at regions between adjacent teeth of a user and for vibrating regions of the mouth of the user between teeth and gums. The cleaning and vibrating are done in a safe, painless, convenient, efficient and economical manner.

First provided in the alternative embodiment is a handle 114 in a generally cylindrical configuration. The handle has a distal end 116 and a proximal end 118 and an exterior surface 120 between the distal and proximal ends. A vibration generating drive mechanism 122 is adapted to be powered by a battery within the handle. The sonic ranges of the vibrating are, preferably, as described above.

Further in this embodiment, operational components are provided on the handle. The operational components include an ON/OFF button 126 adapted to be depressed to inactivate the system and to activate the system at any one of a plurality of speeds. A plurality of lights 128F, 128S and 128I function to indicate the speed as slow, fast, and intermittent. The operational components also include a vibrating coupler 132 adapted to vibrate rapidly during use upon depressing the ON/OFF button.

Next provided in this embodiment is a coupling head 136 in a generally cylindrical configuration. The coupling head has an enlarged distal end 138 and an enlarged proximal end 140. The coupling head has an exterior surface 142 between the enlarged distal and enlarged proximal ends. The enlarged proximal end is formed with a coupling recess 144 for receiving the vibrating coupler 132. The enlarged distal end is formed with a planar surface forwardly and a curved surface rearwardly. The curved surface is formed with a transversely extending coupling recess 146 in a linear configuration.

Next provided in this embodiment is a replaceable holder 150. The replaceable holder has a central base 152 and two outwardly extending fingers 154. The central base is frictionally received in the coupling recess. The fingers have free ends. A piece of floss 156 is secured between the free ends. The central base 152 has the reciprocal linear shape of the rearwardly facing coupling recess 146 to which the holder will be removably received. The head and the holder are fabricated of a plastic material with limited flexibility and resilience whereby applying pressure to the central base of the holder toward the retentive coupling recess 146 of the head will couple and secure the holder with respect to the head. Applying pressure in an opposite direction to the free ends of the fingers will allow uncoupling of the holder with respect to the head. The fingers are spaced from each other by between 0.50 and 1.00 inches. The floss is spaced from the base of the holder by between 0.40 and 0.75 inches thus allowing the teeth to be placed between the fingers. The floss is to be positioned between teeth. Thus vibrating energy is focused to affect the floss as it is positioned between the teeth.

Lastly, in this embodiment, a compressible surface 160 extends from the planar surface of the base between the fingers. The compressible surface is fabricated of an elastomeric material in a rectilinear configuration, the compressible surface having a length of between 0.125 and 0.250 inches. The compressible surface is adapted to contact the surface of the teeth being flossed and to thereby function as a stop to control the depth of penetration and movement of the floss between the teeth while the ON button has been depressed and the head is vibrating during flossing.

FIGS. 13-16 illustrate the primary preferred embodiment 200 of the invention which includes various inventive features. One aspect is the tension free floss 204. The tension free floss is attached between the fingers 206, 208 as in the prior embodiments. This has safety and functional design elements: 1) safety—tension free floss minimizes trauma to the soft tissue between teeth by eliminating the cutting effect that can be attributed to normal flossing technique with highly taught floss or taught flossing devices and 2) functional—tension free floss allows you to form a proper "C" shape with the floss as it cleans the inter-proximal surface of the tooth, as the inter-proximal surfaces of teeth are curved thus requiring floss that can be adapted to a curved surface. It also minimizes the shredding and tearing of the floss as it moves through inter-proximal contact points, which is a common problem associated with using taught floss. The tension free floss is illustrated with the compressible stop 210. In the preferred embodiment, the fingers are spaced between 0.5 and 1.0 inches. The floss is spaced from base of holder between 0.40 and 0.75 inches, preferably 0.30 and 0.75 inches. The compressible stop having a length of 0.125 and 0.250 inches, prefer 0.1 and 0.3 inches.

Figure 17:
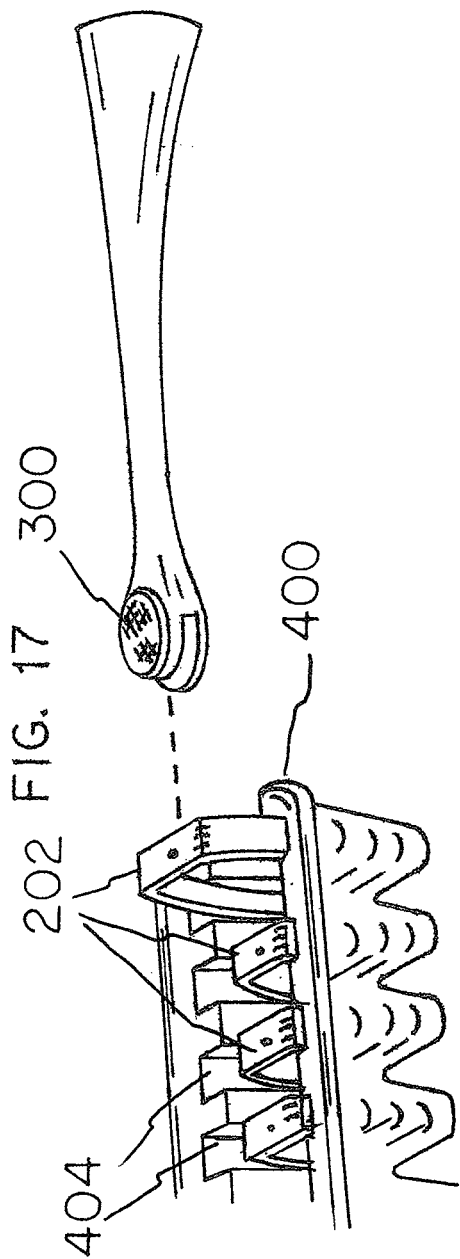
FIG. 17 is perspective illustration of a magazine removably receiving a plurality of replaceable holders for coupling with the coupling head.

A further feature of the preferred embodiment is the bite bumper 300 illustrated in FIGS. 13, 14 and 17. The bite bumper is formed as a soft rubber pad opposite the compressible stop. The bite bumper has two functions: 1) to allow for gentle biting pressure to be applied to the flossed head by opposing teeth to help move the floss between extremely tight contacts. Trauma from this movement is virtually impossible as the opposing compressible stop keeps the floss from traumatizing the soft tissue and 2) to act as a soft bumper for the back side of the flossed head to protect opposing teeth when floss is being removed from between tooth contacts.

A further feature of the present invention is a magazine 400 with recesses 404 for replacement holders 202 functioning as flossers. Note FIG. 17. The magazine of replaceable holders has two primary purposes: 1) to act as a container to store the replaceable flossers and 2) to allow for the easy and proper connection and disconnection of the flossers to the coupling head.

FIGS. 13, 18 and 19 illustrate an additional feature, a manual handle 500. In the event that electrical power is not available for providing the sonic movement through the powered handle, a manual handle 500, not powered, is utilized. This embodiment offers users all of the advantages of the powered handle with the exception of the sonic energy. It is beneficial for those who need a smaller alternative for traveling or for those who prefer a manual movement device over a powered device.

The final feature of the invention is an optional tooth brush 600. Note FIG. 19. Such tooth brush has a distal end with a fitment and coupling design to allow it to be attached to either the powered or manual handle.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A flossing system comprising:
   a handle having a distal and proximal ends and a drive mechanism;
   operational components on the handle including ON and OFF controls and a vibrating coupler to create sonic vibrations of from 150 to 300 Hz;
   a coupling head having a distal and a proximal ends, the proximal end being formed with a coupling recess;
   a replaceable holder having a central base and two outwardly extending fingers, the fingers having free ends with a piece of floss secured there between, the central base having a shape for coupling to and uncoupling from the coupling head, the length of the floss between the fingers being from 5 to 10 percent greater than the distance between the fingers, the floss being spaced from the central base by from 0.30 inches to 0.75 inches;

a compressible stop on the base of the holder between the fingers, the compression stop having an undulating surface with a length from 0.125 inches to 0.250 inches, said undulating surface having a four fin configuration to specifically allow for greater depth of floss movement between the fins when flossing regions between anterior teeth that are longer and narrower in form and function, while also maintaining proper dimension as a whole when compressed between posterior teeth that are broader in form and function, the remainder of the fingers being devoid of a compressible stop; and a bite bumper formed as a soft rubber pad opposite the compressible stop, the bite bumper has two functions: to allows for gentle biting pressure to be applied to the replaceable holder by opposing teeth to help move the floss between extremely tight contacts and to act as a soft bumper for the back side of the replaceable holder to protect opposing teeth when floss is being removed from between tooth contacts.

2. The system as set forth in claim 1 and further including:

a magazine (400) of replacement holders functioning as flossers, the magazine of replaceable holders has two primary purposes: to act as a container to store the replaceable holders and to allow for the easy and proper connection and disconnection of the replaceable holders to the coupling head.

3. The system as set forth in claim 1 and further including:

a manual handle (500) having a proximal end with grip and a distal end with a projection, the projection being shaped to removably receive a replaceable holder.

4. The system as set forth in claim 3 and further including:

a tooth brush attachment having a distal end adapted to couple with both the powered and manual handle.

5. A flossing system (10) (110) for cleaning teeth at regions between adjacent teeth of a user and for vibrating regions of the mouth of the user between teeth and gums, the cleaning and vibrating being done in a safe, painless, convenient, efficient and economical manner, the system comprising, in combination:

a handle (14) (114) in a generally cylindrical configuration and having a distal end (16) (116) and a proximal end (18) (118) and an exterior surface (20) (120) between the distal and proximal ends, a vibration generating drive mechanism (22) (122) and a battery within the handle;

operational components on the handle, the operational components including an ON button (26) (126) and an OFF button (28) (126) and an IN-USE light (30) (128F) (128I) (128S) on the exterior surface of the handle adjacent to the distal end, the operational components also including a vibrating coupler (32) (132) adapted to vibrate rapidly during use upon depressing the ON button;

a coupling head (36) (136) in a generally cylindrical configuration and having an enlarged distal end (38) (138) and an enlarged proximal end (40) (140) and an exterior surface (42) (142) between the enlarged distal and enlarged proximal ends, the enlarged proximal end being formed with a coupling recess (44) (144) for receiving the vibrating coupler (32) (132), the enlarged distal end being formed with a planar surface forwardly and a hemispherical surface rearwardly, the hemispherical surface being formed with a transversely extending coupling recess (46) (146) in a retentive configuration to removably receive the central base (52) (152) of the replaceable holder (50) (150) existing as its reciprocal in shape;

a replaceable holder (50) (150) having a central base (52) (152) (202) and two outwardly extending fingers (54) (154), the fingers having free ends with a piece of floss (56) (156) (204) secured between the free ends, the central base (52) (152) (202) having the reciprocal retentive shape of the rearwardly facing transverse recess (46) (146) to which the holder will be removably received, the head and the holder being fabricated of a plastic material with flexibility and resilience whereby applying pressure to the central base of the holder toward the retentive recess (46) (146) of the head will couple and secure the holder with respect to the head and whereby applying pressure in an opposite direction to the free ends of the fingers will allow uncoupling of the holder with respect to the head, the fingers being spaced from each other by between 0.50 and 1.00 inches, the floss being spaced from the base of the holder by between 0.40 and 0.75 inches, the distance between the fingers adjacent to the ends being from 0.5 to 1.0 inches, the length of the floss between the fingers being from 5 to 10 percent greater than the distance between the fingers thereby allowing the teeth to be placed between the fingers, the floss to be positioned between teeth, and thus the focused vibrating energy to effect the floss as its positioned between the teeth; and a compressible stop (60) (160) extending from the planar surface of the base between the fingers, the compressible stop having a length of between 0.125 and 0.250 inches, the compressible stop adapted to contact the surface of the teeth being flossed and to thereby function to control the depth of penetration of the floss between the teeth while the ON button has been depressed and the head is vibrating during flossing, the fingers being devoid of compressible stops except for the compressible stop extending from the planar surface of the base between the fingers whereby axial movement of the floss is limited solely by the fingers;

a bite bumper (300) coupled to the replaceable holder in the side thereof opposite the fingers, the bite bumper having an oval configuration with an exposed surface adapted to be bitten by patient's teeth facing the teeth being flossed to facilitate the penetration of the floss to a maximum depth between teeth being flossed;

a magazine (400) adapted to removably receive and support a plurality of replaceable holders (152) (202), the magazine formed in a rectilinear configuration with ten parallel slots (404), each slot removably receiving and supporting a single replaceable holders for coupling th the handle;

a manual handle (500) having a proximal end with grip and a distal end with a projection, the projection being shaped to removably receive a replaceable holder; and a tooth brush attachment (600) having a distal end adapted to couple with both the powered and manual handle.

\* \* \* \* \*